United States Patent [19]

Rubins

[11] Patent Number: 5,306,228
[45] Date of Patent: Apr. 26, 1994

[54] BRAIN WAVE SYNCHRONIZER

[76] Inventor: Tye Rubins, 2073 Sunset Plz. Dr., Los Angeles, Calif. 90069

[21] Appl. No.: 878,825

[22] Filed: May 5, 1992

[51] Int. Cl.$^5$ .......................................... A61M 21/00
[52] U.S. Cl. ................................................... 600/27
[58] Field of Search ..................................... 600/26–28

[56] References Cited

U.S. PATENT DOCUMENTS

| | | |
|---|---|---|
| 3,882,850 | 5/1975 | Bailin et al. . |
| 4,008,714 | 2/1977 | Silva et al. . |
| 4,315,502 | 2/1982 | Gorges . |
| 4,335,710 | 6/1982 | Williamson . |
| 4,396,259 | 8/1983 | Miller . |
| 4,456,347 | 6/1984 | Stahly . |
| 4,632,126 | 12/1986 | Aguilar . |
| 4,665,926 | 5/1987 | Leuner et al. . |
| 4,834,701 | 5/1989 | Masaki . |
| 4,902,274 | 2/1990 | Gleeson, III . |
| 4,955,389 | 9/1990 | Schneider . |
| 5,036,858 | 8/1991 | Carter et al. . |
| 5,064,410 | 11/1991 | Frenkel et al. . |
| 5,149,317 | 9/1992 | Robinson ............................. 600/27 |

FOREIGN PATENT DOCUMENTS 3823402 1/1990 Fed. Rep. of Germany ........ 600/27

OTHER PUBLICATIONS

"The Science of Light and Sound," by Theta Technologies, Inc., 1991.
"A Flash in the Brain Pan," by Tom McNichol, In Health Magazine, pp. 84–85, Nov., 1991.
"Brain Blasters," Column in Success Magazine, p. 28, Oct., 1991.
Advertisement for Voyager ® Light/sound Generator (undated).
Advertisement for Innerquest ® Brain Wave Synchronizer (undated).
Advertisement for Zygon SuperMind TM "Brainwave Entrainment Computer" (undated).
Advertisement for "Relaxation Dream Medium" system by MasterMind.
"Brain Cocktails," Peter Occhiogrosso, Article in Forbes, pp. 103–107 (undated).
"Altered States," Article in Eastsideweek, Nov. 6, 1991.
"Light & Sound: The Beat of an Ancient Drum," Article in The New Times, Mar. 2, 1992.

Primary Examiner—Lee S. Cohen
Assistant Examiner—J. P. Lacyk
Attorney, Agent, or Firm—Poms, Smith, Lande & Rose

[57] ABSTRACT

A device for inducing the brain waves of a user to assume a predetermined frequency including a playback device, stereo earphones, and at least one light mounted on glasses in front of each eye of the user. Three separate control signals are pre-recorded superimposed onto a single control track. This composite signal is read by the playback device and is decomposed into the separate control signals by filters in a decoder/controller. One control signal drives a first LED and another drives a second LED. The number of sinusoids within the first and second control signal determining the light intensity. The third control signal is passed alternately to two speakers, with the switching between the speakers being controlled by the state of the first and second control signal. Conventional earphones and a conventional tape player may be used. The invention also includes the method according to which the control signals are pre-recorded, played back, filtered, and applied to the lights and speakers.

18 Claims, 3 Drawing Sheets

BRAIN WAVE SYNCHRONIZER

BACKGROUND OF THE INVENTION

1. Field of the Invention

This invention involves an apparatus and a method for inducing desired brain wave frequencies in a user by presenting periodic visual and audio signals, respectively, to the eyes and ears of the user.

2. Description of Related Art

It is well known that the human brain generates periodic electrical signals, commonly referred to as "brain waves." These brain waves range in frequency from about 1 Hz to about 36 Hz and, for ease of reference, are commonly divided into four or more groups. "Beta" waves (12 to 36 Hz) tend to dominate in the brain during normal waking activity; "Alpha" waves (8 to 12 Hz) have been discovered to occur most frequently when the person is relaxed; "Theta" waves (4 to 7 Hz) are most common during periods of sleep or deep meditation and also occur during periods of learning or memory recall; and "Delta" waves (1 to 4 Hz) appear most frequently during periods of the deepest sleep. These ranges of frequencies are approximate, but in general, the dominate brain wave frequency increases with increasing mental activity.

Experiments have indicated that when light is repeatedly flashed into the eyes of a subject within this frequency band, the brain waves of the subject tend to assume the frequency of the flashing. It has also been discovered that such "synchronization" of brain waves may lead to brain seizures in epileptics or in other people who have a history of brain seizures.

On the other hand, other experiments have demonstrated that pulsating light and sound can induce a synchronized pattern of brain waves. There is, furthermore, evidence to indicate that by inducing a subject's brain waves to come within the Alpha range, the subject at least will be able to relax better, and may even be able to learn more quickly and permanently. Many researchers also report that subject whose brain waves are caused to synchronize within the Alpha range or lower are better able to receive subliminal or audible audio messages.

Differential audio frequencies have also been shown to cause similar effects. For example, if the frequency of a tone played into one ear of a subject is 10 Hz higher than the frequency of a tone played into the subject's other ear, experimental evidence indicates that the subject's brain, acts in a way similar to a "heterodyne," tends to generate brain waves at a frequency approximately equal to the difference in frequency between the two tones, that is, in this case, 10 Hz. The same result arises when tones are alternately put to the left and right ears with a frequency equal to the desired synchronization frequency.

There are accordingly many devices now available that are designed to present flashing lights, alternating tones, or both, to the eyes and ears of a user. Some devices use "bio-feedback," in which the brain wave frequency of the user is sensed and used to control the frequency of the flashing lights or pulsating tones; the user herself thereby attempts to train herself to produce the desired frequency, which is reinforced by the flashing lights and pulsating tones. Many other devices, which do not measure the brain waves in an attempt to create a feedback loop, actively control the flashing or switching frequency. Examples of such devices are described in the following U.S. Patents.

| U.S. Pat. No. | Inventor(s) | Issue Date |
|---|---|---|
| 5,064,410 | Frenkel, et al. | Nov. 12, 1991 |
| 5,036,858 | Carter, et al. | Aug. 6, 1991 |
| 4,955,389 | Schneider | Sept. 11, 1990 |
| 4,902,274 | Gleeson, III | Feb. 20, 1990 |
| 4,834,701 | Masaki | May 30, 1989 |
| 4,665,926 | Leuner et al. | May 19, 1987 |
| 4,632,126 | Aguilar | Dec. 30, 1986 |
| 4,456,347 | Stahly | June 26, 1984 |
| 4,396,259 | Miller | Aug. 2, 1983 |
| 4,335,710 | Williamson | June 22, 1982 |
| 4,315,502 | Gorges | Feb. 16, 1982 |
| 4,008,714 | Silva et al. | Feb. 22, 1977 |
| 3,882,850 | Ballin et al. | June 13, 1975 |

All of these known devices create the synchronizing pulsed light and/or sound by actively generating an electrical pulse at the desired frequency. This electrical synchronization pulse activates a small set of lights in front of the user's eyes, and controls a tone generator whose signal is fed into earphones. In many of these known devices, the electrical pulses result from a timing program in the memory of a microprocessor or a computer. In some of these devices, the user herself selects the synchronization frequency. In other devices, one or more frequencies or programs of varying frequency are generated automatically, whereby the user, in some cases, can select which program she wishes to follow.

The foremost drawbacks of known devices for synchronizing brain waves are that these devices are complicated and expensive. They typically contain many mechanical and electrical components that require careful testing and calibration. Few are suitable for easy use by most individuals, and fewer still are within their budgets. Even the least expensive of these known devices sells at retail for prices on the order of hundreds of dollars.

In order to reduce complexity, at least one device (see the Gleeson patent) encodes control signals on magnetic tape. Such devices, however, typically require four or more audio channels simultaneously, so that they are not suitable for use in common 2-channel devices such as the portable stereo cassette tape players already owned by a large section of the population. Furthermore, the Gleeson device requires special conditioning circuitry separate from the tape player in order to drive the lights and speakers used; this increases design costs.

It is therefore an object of this invention to provide a device for inducing synchronized brain waves using both flashing lights and pulsating tones that is easy to use and that can be manufactured from inexpensive and compact components so as to make it much more affordable than existing devices.

SUMMARY OF THE INVENTION

The invention includes a playback device, stereo earphones, and at least one light mounted on glasses in front of each eye of the user.

In the instant invention, first, second and third control signals are pre-recorded superimposed onto a single control track. The playback device, which may be a conventional tape player, reads the control track, and the corresponding electrical composite signal is transmitted via standard connectors to a decoder/controller.

The decoder/controller includes one filter (preferably band-pass) for each of the three control signals.

The first control signal, after filtering and extraction from the composite signal goes to an operational amplifier (Op Amp), the construction of which is well known within the art. The Op Amp drives a light. The second control signal drives a second light in a similar manner. The intensity of illumination of the lights is controlled by varying the number of sinusoids in the respective control signal.

The first and second control signals are recorded as "bursts", with a non-zero frequency during active period portions and an amplitude of substantially zero during inactive period portions. The state of each signal controls the states of speaker switches that alternately pass the third control signal to left and right speakers or to both speakers depending on the state of the respective signal. Conventional earphones and a conventional tape player may be used.

The invention also includes the method according to which the control signals are pre-recorded, played back, filtered, and applied to the lights and speakers.

DESCRIPTION OF THE PREFERRED EMBODIMENTS

Figure 1:
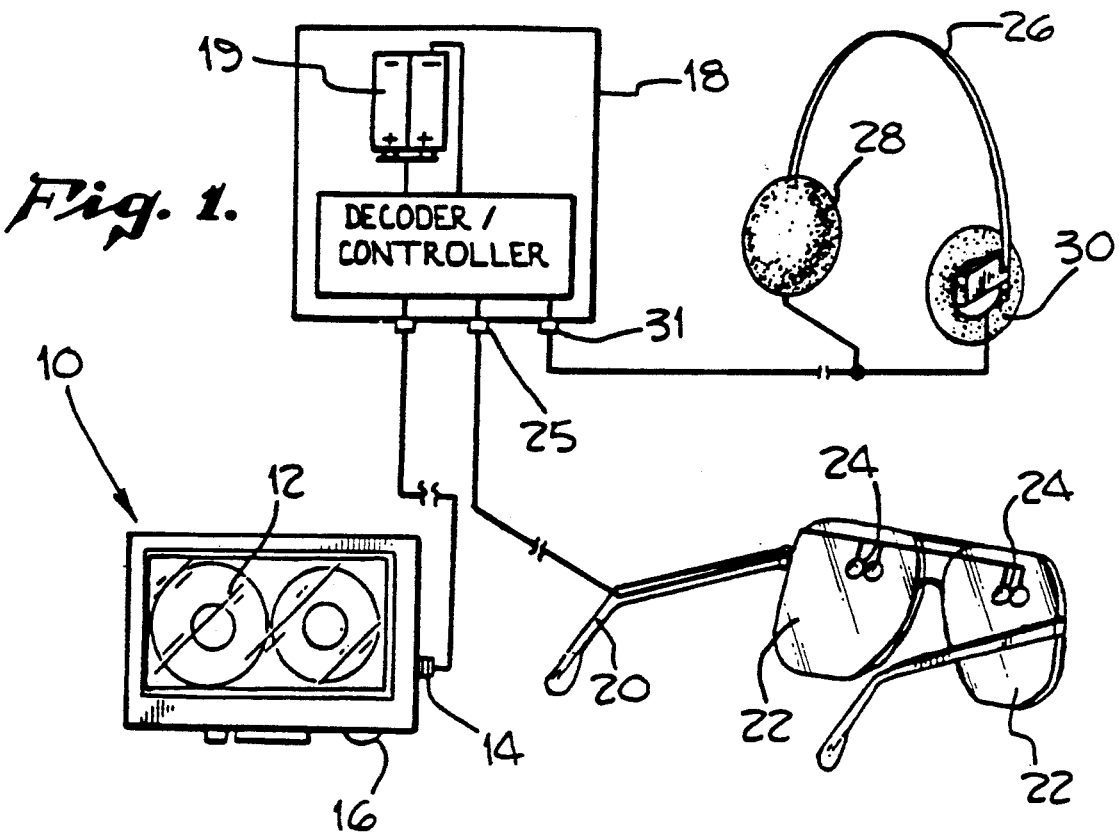
FIG. 1 illustrates the main components and general configuration of the brain wave synchronizer according to the invention.

FIG. 1 shows the main components of the system according to the invention. A standard, commercially available tape player is indicated generally by reference number 10. A standard cassette tape is indicated by reference number 12. The tape player 10 includes a least one audio output 14 and a volume control 16. It is not necessary according to the invention for the tape player 10 to be portable; instead, any tape player may be used, and application of the invention to other technologies such as reel-to-reel tape players, CD players, and digital audio tape players is also possible. The invention requires only that there be some audio output, for example, the output normally used to connect the tape player to headphones.

According to the invention, the recording medium such as the cassette tape 12 needs one track for recording an audio control signal. If the invention is used in combination with another audio program such as a self-help message or other learning program, the recording medium should have at least one other track for carrying this program. The invention is therefore well-suited for use with a standard stereo cassette tape. Indeed, the invention operates with one, two, or more tracks.

The invention also includes a decoder/controller device 18, whose construction and operation are described below. As FIG. 1 illustrates, the user will normally plug the decoder/controller 18 into the output 14 of the tape player 10. The decoder/controller 18 therefore receives the left and right audio tracks of the stereo output. Either of the left or right track can be used as the control track with the unused track being sent directly to the earphones or speakers. After decoding the control signal (described below), the decoder/controller 18 generates signals that control audio and visual synchronization signals. The decoder/controller 18 also houses one or more standard batteries 19 that provide electric current to the circuitry of the decoder/controller.

In order to present flashing visual signals to the eyes of the user, the invention includes glasses 20 with opaque lenses 22 and at least one light 23, 24 mounted on each lens in front of the eye of the user. The glasses 20 are preferably inexpensive, standard glasses whose lenses are covered with an opaque material. This material may be such as a metallic foil, but is it preferably a printed circuit board, which not only shields the user's eye from ambient light, but also carries standard etched or attached conductors that lead electrical current to the lights.

The lights 23, 24 are preferably pairs of light-emitting diodes (LEDs). Such LEDs draw little electrical current and have a sufficiently fast on/off response that the user can clearly sense that they are flashing at or below frequencies in the lower Beta range. The color of the lights 23, 24 is not essential according to the invention as long as the light is visible. It is not necessary to include two paired lights in front of each of the user's eyes. Paired lights are preferred, however, since they provide a wider field of view than a single LED. This in turn makes the glasses 42 more universally useful and reduces the expense of having to manufacture the glasses with different placement of the lights.

One light per eye may, however, be used if it has sufficiently wide field of view and is sufficiently bright. In this context one should also keep in mind that the user's eyes will usually be closed while she is using the invention, and the flashing of the lights must then be visible through her eyelids.

The glasses 20 are connected to the decoder/controller 18 using a standard electrical connector, jack or plug 25. The number of electrical connectors between the decoder/control and the glasses 20, and why, is explained below.

The invention also includes common stereo earphones with a left speaker 28 and a right speaker 30. The earphones 26 are connected to the decoder/controller using a conventional stereo earphone jack 31.

FIG. 1 illustrates one of the main cost-saving advantages of the invention. Most users will already own a tape player 10 and headphones 26 suitable for use with the invention. Even for those users who do not yet own such equipment, the cost of a satisfactory tape player with accompanying headphones, together with the cost of the decoder/controller 18 and glasses 20 according to the invention, will still be much less than the cost of existing devices designed to synchronize brain waves.

According to the invention, control signals for driving the pulsating lights 23, 24 and alternating audio tones in the earphones 26 are pre-recorded using known recording equipment onto a single track of the cassette tape or other recording medium. The control signals in the preferred embodiment comprise a superimposition of three separate audio frequencies onto the control track. These frequencies, labelled f1, f2, and f3 below, are sufficiently separated in the audio range that corresponding band-pass filters (described below) are able effectively to filter out the other two frequencies while passing its center frequency, which is approximately the frequency of the corresponding control tone.

Signals f1 and f2 are pulsating sine waves. During the recording process, the rate of pulsation is equal to the desired brain wave frequency ("pulse"). Each pulse's beginning and ending is determined by a preprogrammed or manually operated sequencer, the construction of which is well know within the art. Furthermore, the number of sinusoids within each pulse can be changed, during the recording process, to control the intensity of illumination of the lights, as is explained below. Furthermore, since f3, which is also a sine wave, will be used as the audio tone in the earphones 26, f3 should be chosen to be comfortable to listen to; frequencies within one octave on either side of middle C are, for example, suitable.

Figure 2:
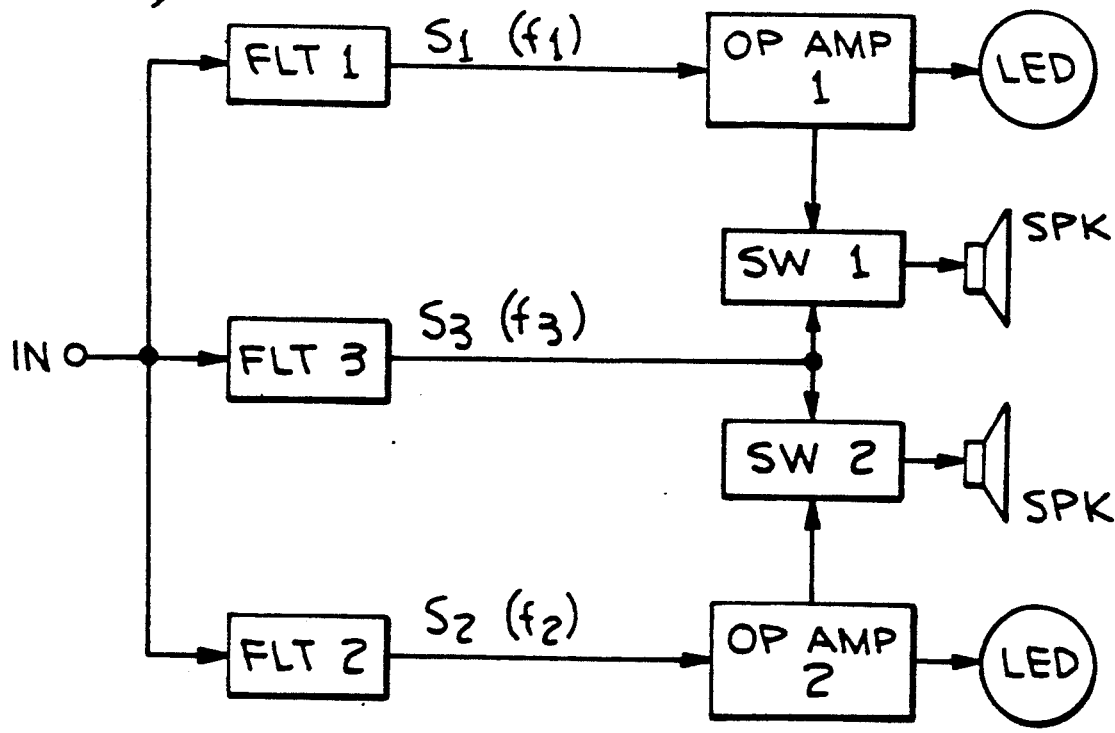
FIG. 2 is a simplified block diagram of the decoding and control circuitry used in the invention.

FIG. 2 is a block diagram that shows the general structure of the circuitry of the decoder/controller 18. The audio input signal from the control track of the cassette tape is indicated at the left as the signal IN. The signal IN first passes to a bank of three filters FLT1, FLT 2, and FLT 3. The output signals from the filters FLT1, FLT 2, and FLT 3 are S1, S2, and S3, respectively. The dominant (and for an ideal band-pass filter, the only, frequency of each output signal S1, S2, and S3 is f1, f2, and f3, respectively. In the preferred embodiment, the filters are band-pass filters, although a low-pass only filter may be used to extract the lowest-frequency control signal from the input signal IN.

Output signals S1 and S2 are both sine waves and are both used in three ways. First, signals S1 and S2 are used to switch on and off LED1 and LED2, respectively. Each signal, S1 or S2, goes to a separate and identical Op Amp. The Op Amp activates a light. Since the frequency of both S1 and S2 is greater than the frequency of the desired brain waves pulse, i.e. greater than 40 Hz and the threshold of human visual perception, the light appears to be on continuously during each pulse.

Second, signals S1 and S2 are used to control the intensity of illumination of the lights. Since the lights are activated, turned on and off, at the same rate as the frequency of the sine waves of S1 and S2, removal of any of the sinusoids from either signal during the recording process will reduce the number of sinusoids going to the respective Op Amp and activating the lights. While the pulse remains unchanged, the reduction in intensity of illumination of the lights during the pulse is directly proportional to the number of sinusoids removed from the signal during the pulse. In other words, this reduces the number of times the lights are activated during the pulse which means the total illumination over the period is reduced.

Figure 4:
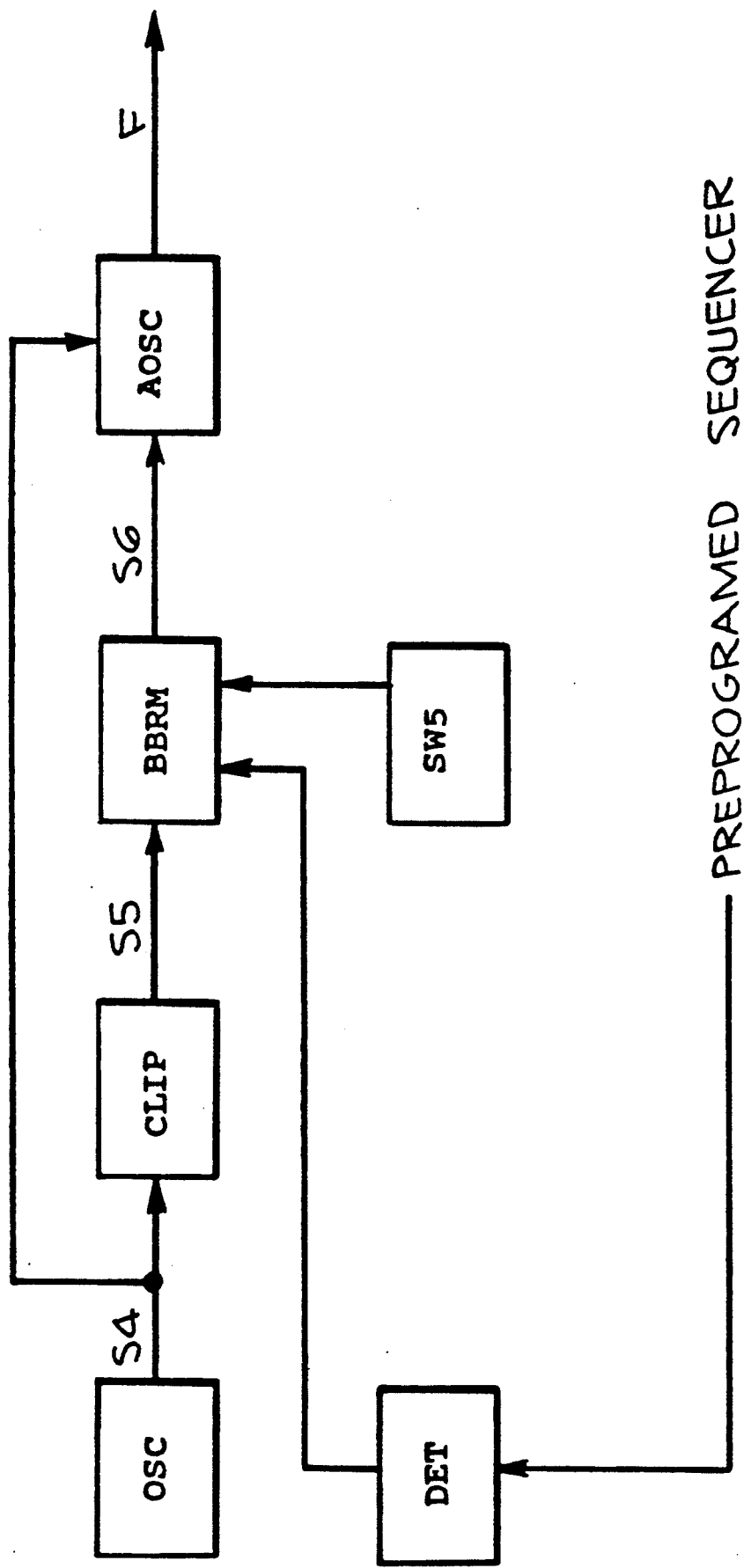
FIG. 4 is a simplified block diagram of the intensity encoding device used in the invention.

The method to accomplish this part of the invention occurs during the recording of F1 and F2 and is illustrated in FIG. 4. An oscillator (OSC) generates a continuous sine-wave tone of 2800 HZ (S4); this is an example only and the tone need not be of this frequency. Signal S4 goes through a clipper (CLIP) which shapes the S4 into square waves (S5). Signal S5 is used as a clock for a binary bit-rate multiplier (BBRM). The preprogrammed sequencer activates a detector (DET) which determines the beginning and ending of each pulse. This information goes to the BBRM which pulses signal S6 on and off at the desired brain wave frequency or pulse. A binary switch (SW5) controls the BBRM and determines the number of square waves that will be in each pulse of S6. The signal S6 goes to an analogous sine wave oscillator (AOSC) which produces the signal to be recorded, F (f1 or/and f2). To produce both f1 and f2 with dissimilar or alternating pulsation rates, two such devices as described above would be required. The construction of the above is well-know within the art.

Third, signals S1 and S2 are also used according to the invention to control the switching from one ear to the other of an audio tone into the earphones,(SPK1 and SPK2). This audio tone itself is carried by the third signal S3 and is present at switches SW1 and SW2. The presence of S1 and S2 activates switches SW1 and SW2, respectively. The activation of either SW1 or SW2 passes S3 to SPK1 or SPK2, respectively.

Although not necessary according to the invention, the third signal S3 preferably includes two frequency components that differ in frequency by an amount equal to the desired brain wave frequency. For example, if the base frequency of the audio tone in the earphones is chosen to be 440 Hz (middle A) and the desired brain wave frequency is 10 Hz (in the Alpha range) the second frequency component of S3 would be chosen to be 440 Hz±10 Hz.

As is mentioned above, experimental results indicate that the human brain "cancels out" or "heterodynes" the frequencies and responds as if it were subject to the differential frequency. Since the frequency difference will in all cases be small (less than approximately 36 Hz, since the desired brain wave frequency will normally be in the Beta range or lower), both of these frequencies will normally fall easily within the pass-band of the third filter FLT3. It is not necessary to include two frequency components in the signal S3 if no "heterodyning" effect is sought. Rather, S3 may then be a simple single-frequency audio tone.

Figure 3:
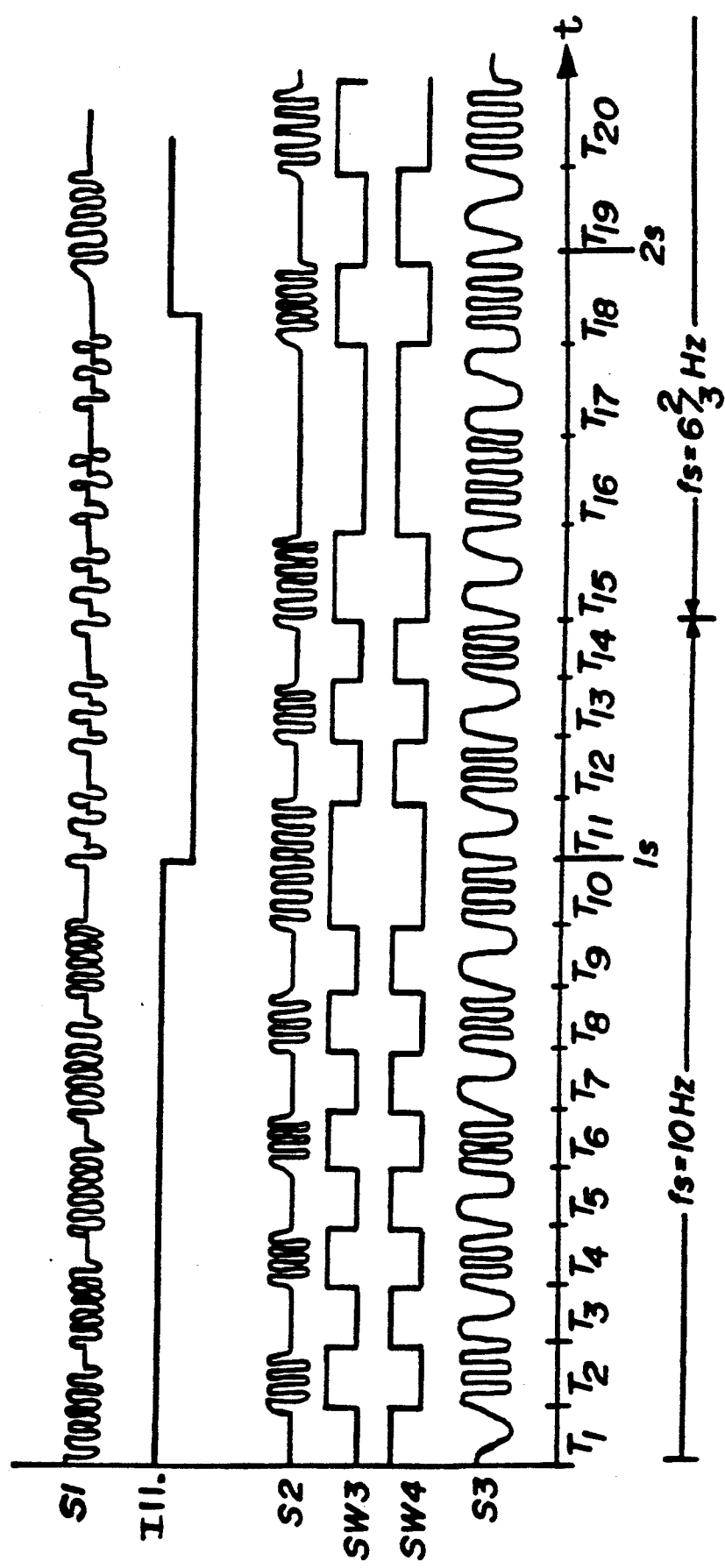
FIG. 3 illustrates graphically a simplified example of the structure and sequencing of a three-tone audio control track used as an input to the decoding and control circuitry.

FIG. 3 illustrates graphically an example of a portion of a time history of various signals in the circuit according to the invention. FIG. 3 does not show precise wave forms or amplitudes, but is rather a simplified, qualitative illustration of the timing and general relationship of the signals. According to the invention, signals S1, S2 and S3 are pre-recorded using known recording equipment onto a single track of the recording medium. Signal S3 is recorded directly. Signals S1 and S2 are processed prior to recording to make the number of sinusoids within each pulse proportional to the percent illumination desired. In FIG. 3, these signals are shown separately, that is, after separate filtering. On the control track of the recording medium, these three signals are superimposed on each other to form a single-track, multi-control signal.

One significant advantage of this invention is therefore that it is not necessary to provide special signal generators, timing circuitry, or specialized microprocessor programming in any component that the user would have to buy in order to use the invention; instead, all necessary control signals are generated in a recording studio, and can then be put easily on a large number of inexpensive standard cassette tapes. Furthermore, the number of different synchronization routines is not limited to some predetermined and pre-programmed set, but rather may be varied for all users simply by mass recording of a new routine onto cassette tapes that can be made available to all at low cost.

In FIG. 3, the left portion of the horizontal time axis is divided into fourteen 1/10th second intervals T1-T14. Since the period is equal to the inverse of the frequency, the synchronization frequency $f_s$ in these intervals is 10 Hz (in the Alpha range). This is chosen by way of example only. After the fourteen 1/10th second period, it is assumed, also by way of example, that the synchronization frequency $f_s$ is to drop to 6⅔ Hz, corresponding to a signal period of 15/100 seconds. Six such period T15-T20 are illustrated in FIG. 3.

The second signal S2 controls the flashing of the second light LED2. Over the first ten periods T1-T10 S2 is present when S1 is absent. This means that the two lights LED1 and LED2 flash alternately. This is not necessary according to the invention. Rather, during the intervals T11, T13, and T15, S1 and S2 are synchronized, so that the lights will flash simultaneously. Since S1 and S2 are independent of each other, any pattern of flashing can be create simply by recording the two signals S1 and S2 with the desired sequencing.

The signal S3 determines the audio tone that the user will hear in the earphones or speakers SPK1 and SPK2. In the example shown in FIG. 3, the signal S3 alternates between two frequencies. This frequency shift is optional according to the invention, but if it is used, the frequency difference should preferably be equal to the desired synchronization frequency $f_s$. (In FIG. 3, the wave form for signal S3 is illustrated in greatly simplified form for the sake of clarity; for a base tone of 440 Hz, for example, signal S3 will go through 44 full cycles during each interval T1 through T10.) In the example shown in FIG. 3, the signal S3 has its higher frequency during each even-numbered time interval (T2, T4, T6, etc.) and its lower frequency during each odd-number interval. The signal S3 is recorded easily using known signal synthesizers and recording equipment.

During the first ten periods T1-T10 of the example illustrated in FIG. 3, the user will see lights that flash alternately left-right at a frequency of 10 Hz, and will hear a tone that switches back and forth between the left and right ears at a frequency of 10 Hz. Additionally, the tone heard in the one ear will be 10 Hz higher than the tone heard in the other ear.

According to the invention, the intensity of the flashing lights LED1 and LED2 can be controlled and varied according to a predetermined program during the original recording of the control track, for example, on a master tape.

During the time intervals T11-T15, the user Will see lights that flash simultaneously in both eyes, with an intensity less than during the preceding ten intervals. The user will still, however, hear alternating tones of a slightly different frequency from ear to ear. During the time intervals T17-T20, the user will once again see alternating flashing lights at the lower intensity, and will hear alternating tones of slightly different frequency but during these intervals the synchronizing frequency will be lower since the "burst" and "pause" periods of the signals S1 and S2 are longer than during the first ten time intervals. Of course, in actual use a given frequency of lights and tones will normally continue for much longer than is illustrated in FIG. 3, but they do not necessarily have to do so; any pattern is possible by suitable pre-recording of the control signals S1, S2, and S3. As is mentioned above, the frequencies of the control signals S1, S2, and S3 should be separated sufficiently so that each filter FLT1, FLT2, and FLT3 will be able to reject that two control signals other than the control signal at or near its center frequency.

One advantage of the invention is that most of the components in the decoder/controller are readily available in the market and are inexpensive. Furthermore, components such as the active filters are readily available as small, inexpensive, integrated circuits incorporated into single chips. This helps to keep the decoder/controller both small and affordable. No signal generation circuitry is required, since the frequencies and timing of the control signals are arranged in advance during the recording of the control track of the cassette tape.

By centralizing the control function to the original recording studio that makes a master tape, no separate expensive microprocessor-controlled signal generation is required by the user.

Note that the playback speed of standard cassettes, compact discs, etc., is standardized, so that a control or audio signal recorded at, say, 5 Hz will not be "stretched" or "compressed" significantly during playback. Furthermore, the frequency of the "bursts" (typically at the synchronization frequency) will not change substantially if the tape speed is kept within the limits normally found in conventional tape players.

I claim:

1. An arrangement, including earphones having first and second speakers and a stereo connector, for inducing brain waves with a predetermined synchronization frequency in the brain of a user, comprising:

a recording medium with a dingle, pre-recorded control track;

a playback device being arranged to read the control rack and to generate an electrical composite control signal corresponding to the control track;

a decoder/controller including a first filter with an output comprising a first filtered control signal, a second filter with an output comprising a second filtered control signal, and a third filter with an output comprising a third filtered control signal, with each filter having the composite control signal as an input signal;

a first connector means for connecting the playback device electrically with the decoder/controller;

a visual presentation means for screening the eyes of a user from ambient light;

a second connector means for connecting the visual presentation means electrically with the decoder/controller;

first and second light, each mounted on the visual presentation means so as to be in front of a respective one of the eyes of the user;

a light-switching means for activating the first and second lights at a synchronization frequency when selected ones of the filtered control signals have a substantially non-zero amplitude, said light-switching means including a first amplifier that is electrically connected to the first light and a second amplifier that is electrically connected to the second light;

a sound-switching means for applying a selected one of the filtered control signals alternately to the first and second speakers of the earphones and for producing audible tones pulsating at the synchronization frequency;

the sound-switching means includes a first amplifier that is electrically connected to a first switch and a second amplifier that is electrically connected to a second switch;

the first filter is connected to the first amplifier;

the second filter is connected to the second amplifier;

the third filter is connected to inputs of the first and second switches;

the first and second speakers are connected to outputs of the first and second switches, respectively; and, encoder means for varying, during recording of the first and second control signals, the number of sinusoids in the first and second control signals.

2. An arrangement, including earphones having first and second speakers and a stereo connector, for inducing brain waves with a predetermined synchronization frequency in the brain of a user, comprising:

a recording medium with a single, prerecorded control track;

a playback device being arranged to read the control track and to generate an electrical composite control signal corresponding to the control track;

a decoder/controller including a plurality of filters, each filter having the composite control signal as an input signal and generating a corresponding filtered control signal;

a first connector means for connecting the playback device electrically with the decoder/controller;

a visual presentation means for screening the eyes of the user from ambient light;

a second connector means for connecting the visual presentation means electrically with the decoder/controller;

first and second lights, each mounted on the visual presentation means so as to be in front of a respective one of the eyes of the user;

a light-switching means for activating the first and second lights at a synchronization frequency when selected ones of the filtered control signals have a substantially non-zero amplitude; and a sound-switching means for applying a selected one of the filtered control signals alternately to the first and second speaker of the earphones and for producing audible tones pulsating at the synchronization frequency.

3. An arrangement as defined in claim 2, in which: the filters include a first filter for passing a first one of the filtered control signals, a second filter for passing a second one of the filtered control signals, and a third filter for passing a third one of the filtered control signals;

the light-switching means includes a first amplifier that is electrically connected to the first light and a second amplifier that is electrically connected to the second light;

the first filter is connected to the first amplifier and the second filter is connected to the second amplifier;

the first and second lights are connected to the first and second amplifier, respectively;

the sound-switching means includes a first switch that is electrically connected to the first speaker and a second switch that is electrically connected to the second speaker; and the first amplifier is connected to the first switch and the second amplifier is connected to the second switch;

third filter is connected to inputs of the first and second switches;

the first and second speakers are connected to outputs of the first and second switches respectively;

whereby, when the first filtered control signal has a positive amplitude, the first switch closes to electrically transmit the third filtered control signal to the first speaker, and when the second filtered control signal has a positive amplitude, the second switch closes to electrically transmit the third filtered control signal to the second speaker.

4. A method for inducing brain waves with a predetermined synchronization frequency in the brain of a subject, comprising the following steps:

A) pre-recording onto a single control track of a recording medium a superimposed, composite control signal including a first control signal, with a first frequency range, a first alternating pattern of active and inactive period portions, and a first quantity of sinusoids, a second control signal, with a second frequency range, a second alternating pattern of active and inactive period portions, and a second quantity of sinusoids, and a third control signal with a third frequency range;

B) varying, during recording, the number of sinusoids in the first and second control signal as a means of varying the intensity of illumination of first and second lights;

C) reading the control track to generate a composite input signal;

D) filtering the composite input signal in a decoder/controller and extracting and separating the first, second and third control signals;

E) applying the first control signal to the first light and applying the second control signal to the second light for activating the lights at a predetermined synchronization frequency;

F) producing an audible tone alter in a first speaker and a second speaker at the predetermined synchronization frequency by applying the third signal to the first speaker during the active period portions of the first signal and applying the third signal to the second speaker during the active portion of the second signal.

5. A method as defined in claim 4, further including the step of pre-recording the third control signal with a base frequency during the active period portions of the second signal and with a deveated frequency during the active portion of the second signal, with the difference between the base frequency and the deviated frequency being equal to the predetermined synchronization frequency.

6. A method as defined in claim 4, further including the step of reducing the intensity of illumination of the lights during recording by proportionally reducing the number of sinusoids in the first and second control signals.

7. An arrangement, including earphones having first and second speakers and a stereo connector, for inducing brain waves with a predetermined synchronization frequency in the brain of a user, comprising:

a recording medium with at least one, prerecorded control track, wherein the track includes a pulsed waveform signal having a frequency greater than a predetermined threshold flicker rate;

a playback device being arranged to read the control track and to generate an electrical control signal corresponding to the control track;

a visual presentation means for screening the eyes of the user from ambient light;

a connector means for connecting the visual presentation means electrically with the playback device;

first and second lights, each mounted on the visual presentation means so as to be in front of a respective one of the eyes of the user;

light-switching means for activating the first and second lights at the predetermined threshold flicker rate when the control signal has a substantially non-zero amplitude; and sound-switching means for applying the control signal to the first and second speaker of the earphones and for producing audible tones.

8. The arrangement according to claim 7, wherein the predetermined threshold flicker rate is approximately 40 Hertz.

9. The arrangement according to claim 8, wherein the recording medium includes a magnetic tape.

10. The arrangement according to claim 9, wherein the first and second lights further comprise a light emitting diode.

11. The arrangement according to claim 10, wherein the pulsed waveform signal further comprises a sinusoidal waveform contained within a period of a pulse.

12. The arrangement according to claim 7, wherein the arrangement further comprises an unitary housing, and the recording medium and the playback device are contained in the unitary housing.

13. The arrangement according to claim 12, wherein the arrangement further comprises an operational amplifier connected to an output of the playback device to receive the electrical control signal, and wherein the first and second lights include diodes connected to and actuated by the operational amplifier.

14. The arrangement according to claim 13, wherein the playback device and the light-switching means operate in synchronism.

15. A brain wave synchronizer for stimulating the brain of a user to obtain a brain wave synchronization frequency, comprising:

a unitary medium containing an audio program and a brain wave synchronization program;

a reader means for reading the audio program and the brain wave synchronization program;

a power source;

a controller means for receiving the audio and brain wave synchronization programs read by the reader means, connected to the power source;

a light emitting device, actuated by the controller means in accordance with the brain wave synchronization program, adapted to be disposed proximal to an eye of the user; and an audio emission device, actuated by the controller means in accordance with the brain wave synchronization program and the audio program, adapted to be disposed proximal to an ear of the user;

whereby the light emitting device and the audio emission device stimulate the user's brain.

16. The brain wave synchronizer of claim 15, wherein the medium further comprises a magnetic recording tape.

17. The brain wave synchronizer of claim 16, wherein the reader means further comprises a magnetic recording tape player.

18. The brain wave synchronizer of claim 17, wherein the light emitting device includes a light emitting diode mounted to an opaque lens of a spectacle frame adapted to be worn by the user, and the audio emission device includes an electromagnetic transducer.

* * * * *